United States Patent
Lee et al.

(10) Patent No.: US 7,024,313 B2
(45) Date of Patent: Apr. 4, 2006

(54) METHOD OF ESTIMATING THE PROPERTIES OF A POLYMER PRODUCT

(75) Inventors: Jin-Seuk Lee, Seosan-shi (KR); Woo-Kyoung Kim, Seonsan-shi (KR); Suek-Ho Kim, Seonsan-shi (KR)

(73) Assignee: Samsung General Chemicals, Co., Ltd., (KR)

( * ) Notice: Subject to any disclaimer, the term of this patent is extended or adjusted under 35 U.S.C. 154(b) by 272 days.

(21) Appl. No.: 10/362,946

(22) PCT Filed: Aug. 21, 2001

(86) PCT No.: PCT/KR01/01415

§ 371 (c)(1),
(2), (4) Date: Jul. 30, 2003

(87) PCT Pub. No.: WO02/16932

PCT Pub. Date: Feb. 28, 2002

(65) Prior Publication Data

US 2004/0038301 A1    Feb. 26, 2004

(30) Foreign Application Priority Data

Aug. 24, 2000 (KR) ................................ 2000-49232

(51) Int. Cl.
*C08F 2/00* (2006.01)
(52) U.S. Cl. .................. 702/30; 700/269; 526/59; 526/65
(58) Field of Classification Search .............. 526/59, 526/65; 702/30; 700/269
See application file for complete search history.

(56) References Cited

U.S. PATENT DOCUMENTS

| 4,620,049 A | | 10/1986 | Schmidt et al. | |
|---|---|---|---|---|
| 5,532,487 A | | 7/1996 | Brearley et al. | |
| 6,093,211 A | * | 7/2000 | Hamielec et al. | ............. 703/12 |
| 6,106,785 A | | 8/2000 | Havlena et al. | |

FOREIGN PATENT DOCUMENTS

WO          97/26549          7/1997

* cited by examiner

*Primary Examiner*—Fred Teskin
(74) *Attorney, Agent, or Firm*—Meyertons, Hood, Kivlin, Kowert & Goetzel, P.C.; Eric B. Meyertons

(57) ABSTRACT

The present invention relates to a method of estimating the properties of a polymer product by using converted process variables (cPV's) which means process variable that final or intermediate product experienced earlier in average in the reactors by stage with respect to the final product, which incorporates residence time distribution to process variables, wherein said method comprises the following steps of: computing cPV's by incorporating the residence time distribution to said process variables by means of theoretically determining the amounts of content and discharge of the product in the process, and then solving the balance equations of a hypothetical substance by taking the respective process variables as those of the hypothetical substance: and estimating the properties of the product by inputting to various property estimation models cPV's in the reactors by stage with respect to the final product after incorporating the residence time distribution to said process variables.

8 Claims, 7 Drawing Sheets

METHOD OF ESTIMATING THE PROPERTIES OF A POLYMER PRODUCT

TECHNICAL FIELD

The present invention relates to a method of estimating the properties of a polymer product, or more particularly to a method of estimating the properties of a product by using converted process variables (cPV's) which means process variable that final or intermediate product experienced earlier in average in the reactors by stage with respect to the final product, which incorporates residence time distribution to process variables, wherein said method comprises the following steps of: incorporating the residence time distribution to said process variables by means of theoretically determining the amounts of content and discharge of the product in the process, and then solving the balance equations of a hypothetical substance by taking the respective process variables as those of the hypothetical substance; and estimating the properties of the product by inputting to various property estimation models cPV's in the reactors by stage with respect to the final product after incorporating the residence time distribution to said process variables.

BACKGROUND ART

Generally, the adjustment of physical properties of polyolefin in a commercial plant is largely dependent on experiences of a skilled operator. However, because of the differences in modes of operations of respective operators, the operations are sometimes inconsistent. The modes of operations which are different from operator to operator affect the physical properties of a product (i.e., uniformity) and in the end, even if the products are of the same grade, there still may be differences depending on the lots. Obviously, this is a potential cause of claims or complaints from the end users.

In order to overcome these problems, it is useful to apply the technology, which allows estimation of properties of a product, at the point of its production.

Conventionally, in estimating the properties of a polymer product, various empirical and statistical models have been mainly used, such as empirical correlation, neural network, or partial least square (PLS) models.

While the correlation models of prior art can be relatively easily applied to the steady states wherein the process conditions are stably maintained, the conventional technology is problematic in that it frequently shows large differences from the actual analysis values in the unsteady states or in a grade change, where the process conditions are in the state of flux.

These differences are due to the existence of a process delay. The process delays are expressed in different forms, depending on the intrinsic residence time distribution of various devices. For example, there is a simple case of a push back to a certain period of time (e.g., in pipes), or there may be a push back of extended effects in the form an exponential function, such as in continuous stirred tank reactors (CSTR). For other reaction devices, there may be other peculiar types of residence time distribution.

In particular, in cases of multi-stage continuous polymer plants, up until to the point that the product would be affected by the extended effects caused by a change in operational conditions of the previous stage, there would be a long time delay, depending on the intrinsic residence time distribution characteristics of the process. Consequently, because of a rather simplistic way of estimating the properties of a polymer product from the process variables of the current states, it would be of course accompanied by a significant degree of error.

Meanwhile, a typical method of estimating the properties of polymers by incorporating the residence time distribution of the process is by means of a physical model. It is a method of establishing balance equations for a substance by way of reaction system and then solving said equations. For this method based on said physical model, it is necessary to obtain reaction rate constants and various types of physiochemical constants. However, there lies the problem since it is not so easy to obtain these types of constants. To solve this problem of physical model, the method widely used in the industry is a method of computing cumulative properties (hereinafter cumulative properties model) by calculating the instantaneous properties of a product, followed by the application of residence time distribution and the mixing rule of polymer properties.

The method according to said cumulative properties model has many advantages, such as easy application to the actual process in some cases, and potential utilization of empirical correlation, neural network, PLS models, etc. in estimation of instantaneous properties. However, with respect to the method of cumulative properties model, there is a problem of requiring "model training," or the data of the steady states for the purposes of carrying out the process of empirical correlation, neural network, or PLS for estimating the properties of a product. In particular, in case of a system with recycle streams which are not maintained constantly by time, it is almost impossible to apply the cumulative properties model.

DISCLOSURE OF THE INVENTION

In order to solve the problems of prior art as above, the present invention seeks to provide a method of applying cPV's in operation in the reactors by stage, such as temperature and pressure, to the models of estimating the properties of a product by processing the process variables by incorporating the residence time distribution to the process variables themselves by way of further simplification of the cumulative properties model which finds cumulative properties by means of residence time distribution and the nixing rule of polymer properties by computing the instantaneous properties from the current values of process variables.

The present invention relates to a method of estimating the properties of a product by using cPV's in the reactors by stage with respect to the final product, which incorporates residence time distribution to process variables, wherein said method comprises the following steps of: computing cPV's in the reactors by stage with respect to the final product by incorporating the residence time distribution to said process variables by means of theoretically determining the amounts of content and discharge of the product in the process, and then solving the balance equations of a hypothetical substance by taking the respective process variables as those of the hypothetical substance; and estimating the properties of the product by inputting to various property estimation models cPV's in the reactors by stage with respect to the final product after incorporating the residence time distribution to said process variables.

Moreover, in relation to the method of monitoring the state of process incorporating the residence time distribution to the process variables, the present invention relates to a method of monitoring the state of process, wherein said method comprises theoretically determining the amounts of content and discharge of the product in the process, and then incorporating the residence time distribution to said process variables by way of the method of solving the balance equations of a hypothetical substance by taking the process variables as those of the hypothetical substance; and monitoring the state of process by inputting to various process-state-monitoring models cPV's in the reactors by stage with respect to the final product after incorporating the residence time distribution to said process variables.

BEST MODE FOR CARRYING OUT THE INVENTION

The present invention is described in further detail with an example as below: Nevertheless, it is described here for illustrative purposes only and does not limit the present invention in any manner.

Figure 1:
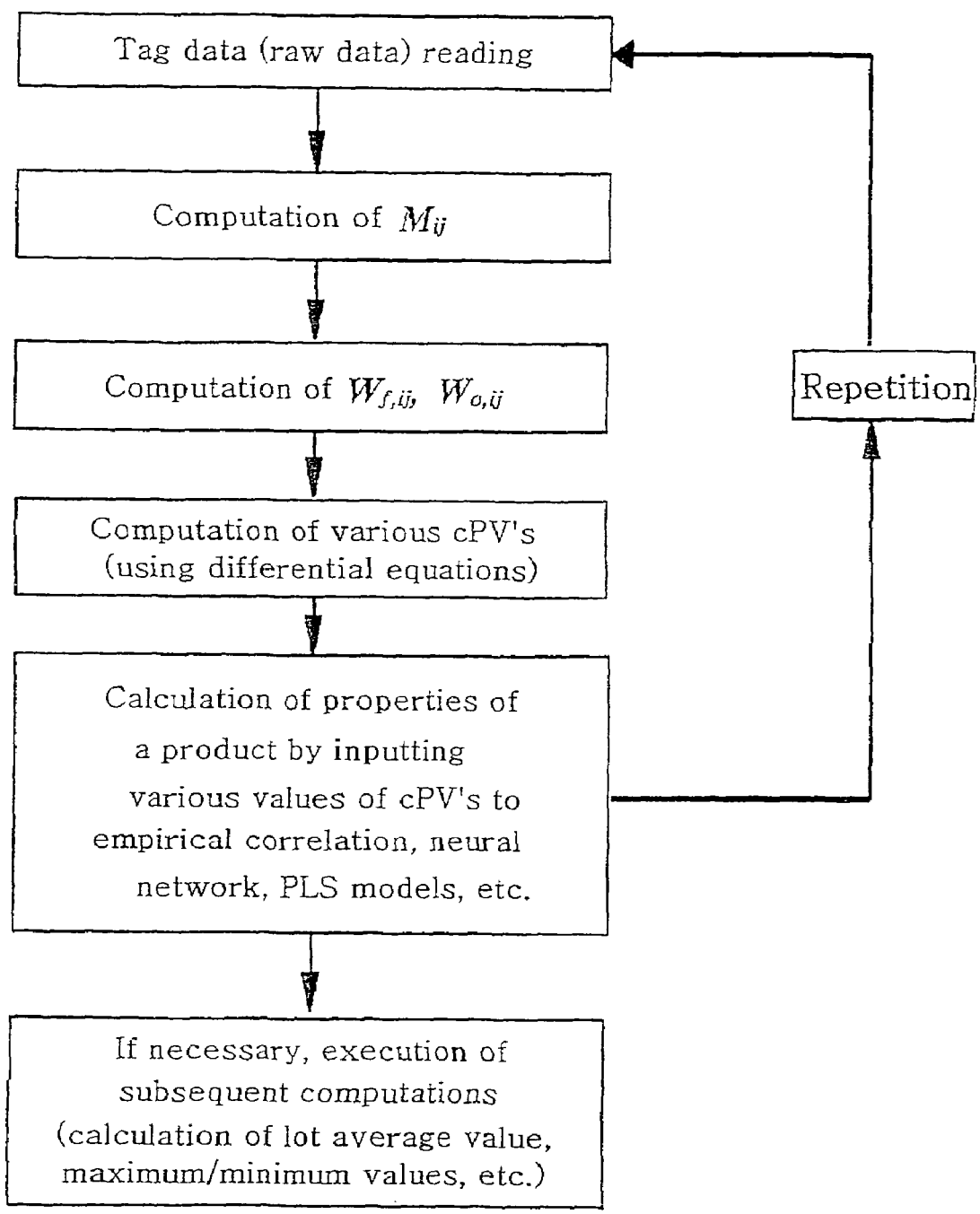
FIG. 1 is a bloc diagram, which illustrates the method of estimating the properties of a polymer product according to the present invention.

FIG. 1 is a bloc diagram, which shows the method of estimating the properties of a polymer product according to the present invention. FIG. 1 shows the process of computing cPV's in the reactors by stage with respect to the final product discharged at a certain time period with a given operational condition of each stage. This computation was made with due consideration of residence time distribution.

The process of computation shown in FIG. 1 is described as below, which computes, with due consideration of residence time distribution, cPV's in the reactors by stage with respect to the final product discharged at a certain time period.

First, the raw data such as reactor temperature, pressure, and concentration were read through a controller, etc. From the raw data read in as such, the balance equations (Mathematical Formulas 1~2 as below) of a substance with respect to the polymers were constructed. From these balance equations of the substance, $M_{ij}$ could be obtained, which is the mass (kg) of the polymers, polymerized in the $i^{th}$ reactor and passed over thereto, out of the polymers in the $j^{th}$ reactor. Next, $W_{f,ij}$ was obtained, which is the mass flow rate (kg/hr) of the polymers, polymerized in the $i^{th}$ reactor, out of the polymers fluxed in into the $j^{th}$ reactor. Then, $W_{o,ij}$ was obtained; which is the mass flow rate (kg/hr) of the polymers, polymerized in the $i^{th}$ reactor, out of the polymers discharged from the $j^{th}$ reactor. The mathematical formulas used herein are as follows:

$dM_{ij}/dt = W_{f,ij} - W_{o,ij} (i \neq j)$  Mathematical Formula 1

$dM_{ii} = W_i - W_{o,ii} (i=j)$  Mathematical Formula 2

$W_{f,ij} = W_{o,ij-1}$  Mathematical Formula 3

$W_{o,ij} = wf_{ij} W_{o,j}$  Mathematical Formula 4

$wf_{ij} = M_{ij}/M_j (i \leq j)$  Mathematical Formula 5

$W_{f,12} = W_{f,2} = W_{o,11} = W_{0,1}$  Mathematical Formula 6

$$\sum_{i=1}^{j} wf_{ij} = 1; \sum_{i=1}^{j} M_{ij} = M_j$$  Mathematical Formula 7

In the above mathematical formulas, the following conventions are used:

$M_i$: Mass (kg) of polymers in the $i^{th}$ reactor;

$W_{f,i}$: Mass flow rate (kg/hr) of polymers of inflow to the $i^{th}$ reactor;

$W_{o,i}$: Mass flow rate (kg/hr) of polymers discharged from the $i^{th}$ reactor;

$w_{f,ij}$: Ratio (kg/kg) of the amounts of polymers, polymerized in the $i^{th}$ reactor, out of the polymers in the $j^{th}$ reactor;

$M_{ij}$: Mass (kg) of polymers, polymerized in the $i^{th}$ reactor and passed over thereto, out of the polymers in the $j^{th}$ reactor;

t: Time (hr);

$W_i$: Polymerization rate (kg/hr) within the $i^{th}$ reactor;

$W_{f,ij}$: Mass flow rate (kg/hr) of polymers, polymerized in the $i^{th}$ reactor, out of the polymers fluxed in to the $j^{th}$ reactor; and $W_{o,ij}$: Mass flow rate (kg/hr) of polymers, polymerized in the $i^{th}$ reactor, out of the polymers discharged from the $j^{th}$ reactor.

The above formulas are rearranged as follows:

$dM_{ij}/dt = M_{i,j-1}/\theta_{j-1} - M_{ij}/\theta_j (i \neq j)$  Mathematical Formula 8

$dM_{ij}/dt = W_i - M_{ii}/\theta_i (i=j)$  Mathematical Formula 9

In the above mathematical formulas, the following conventions are used:

$\theta_i$: Average residence time (hr) in the $i^{th}$ reactor;

$M_{ij}$: Mass (kg) of polymers, polymerized in the $i^{th}$ reactor and passed over thereto, out of the polymers in the $j^{th}$ reactor; and $W_i$: Polymerization rate (kg/hr) within the $i^{th}$ reactor.

Various cPV's were computed by applying the numerical values as obtained above to the balance equations of the hypothetical substance (taking the process variables as those of the hypothetical substance) of various process variables expressed as differential equations. To obtain the properties of a product, various cPV's as computed above were inputted to the empirical correlation, neural network, partial least square models, etc. The process as such was repeated for each unit time.

Moreover, if necessary, the lot average value, lot maximum value, and lot minimum value could be obtained by using the numerical values as computed by using cPV's.

The present invention is now described in further detail with examples with reactor temperature, which is a typical operational condition therein.

By taking the reactor temperature as that of the hypothetical substance, the balance equations of the hypothetical substance as follows could be established:

$$dM_{ij}T_{ij}/dt = W_{f,ij}T_{i,j-1} - W_{o,ij}T_{ij} (i \neq j) \quad \text{Mathematical Formula 10}$$

$$dM_{ii}T_{ii}/dt = W_iT_i - W_{o,ii}T_{ii} (i = j) \quad \text{Mathematical Formula 11}$$

In the above mathematical formulas, the following conventions are used:

$M_{ij}$: Mass (kg) of polymers, polymerized in the $i^{th}$ reactor and passed over thereto, out of the polymers in the $j^{th}$ reactor;

$T_i$: Temperature (° C.) in the $i^{th}$ reactor;

$T_{ij}$: Of the polymers in the $j^{th}$ reactor (or discharged), the average temperature (° C.) in the $i^{th}$ reactor, experienced by the portion produced in the $i^{th}$ reactor;

t: Time (hr);

$W_i$: Polymerization rate (kg/hr) within the $i^{th}$ reactor;

$W_{f,ij}$: Mass flow rate (kg/hr) of polymers, polymerized in the $i^{th}$ reactor, out of the polymers fluxed in to the $j^{th}$ reactor; and $W_{o,ij}$: Mass flow rate (kg/hr) of polymers, polymerized in the $i^{th}$ reactor, out of the polymers discharged from the $j^{th}$ reactor.

Of the polymers in the $j^{th}$ reactor (or discharged), if $T_{cum,ij}$ were taken to be the temperatures experienced in the $i^{th}$ reactor by all of the polymers produced from the first reactor to the $i^{th}$ reactor, the formulas must be changed as follows:

$$d\sum_{k=1}^{i} M_{kj}T_{cum,ij}/dt = \sum_{k=1}^{i} W_{f,kj}T_{cum,i,j-1} - \sum_{k=1}^{i} W_{o,kj}T_{cum,ij} (i \neq j) \quad \text{Mathematical Formula 12}$$

$$d\sum_{k=1}^{i} M_{ki}T_{cum,ii}/dt = dM_iT_{cum,ii}/dt = W_{j,i}T_{cum,i-1,i-1} + W_iT_i - W_{o,i}T_{cum,ii} \quad \text{Mathematical Formula 13}$$

In the above mathematical formulas, the followings conventions are used:

$T_{cum,ij}$: Of the polymers in the jth reactor (or discharged), the temperatures (° C.) experienced in the $i^{th}$ reactor by all of the polymers produced from the first reactor to the $i^{th}$ reactor;

$M_{ij}$: Mass (kg) of polymers, polymerized in the $i^{th}$ reactor and passed over thereto, out of the polymers in the $j^{th}$ reactor;

$W_{f,i}$: Mass flow rate (kg/hr) of polymers of inflow to the $i^{th}$ reactor;

$M_i$: Mass (kg) of polymers in the $i^{th}$ reactor;

$W_{f,ij}$: Mass flow rate (kg/hr) of polymers, polymerized in the $i^{th}$ reactor, out of the polymers fluxed in to the $j^{th}$ reactor;

$W_{o,ij}$: Mass flow rate (kg/hr) of polymers, polymerized in the $i^{th}$ reactor, out of the polymers discharged from the $j^{th}$ reactor;

$W_{o,i}$: Mass flow rate (kg/hr) of polymers discharged from the $i^{th}$ reactor;

$W_i$: Polymerization rate (kg/hr) within the $i^{th}$ reactor; and $T_i$: Temperature (° C.) in the $i^{th}$ reactor.

Of course, in case of reaction temperature, among two of the mathematical formulas of Mathematical Formulas 10~11 and 12~13, the forms of Mathematical Formulas 10~11 should be used to confer some physical meaning therein. Depending on the characteristics of process variables, there should be appropriate selections for use among Mathematical Formulas 10~11 or 12~13.

After going through the procedures as above, the instantaneous operational conditions and cPV's at each stage of the production point could be computed.

Figure 2:
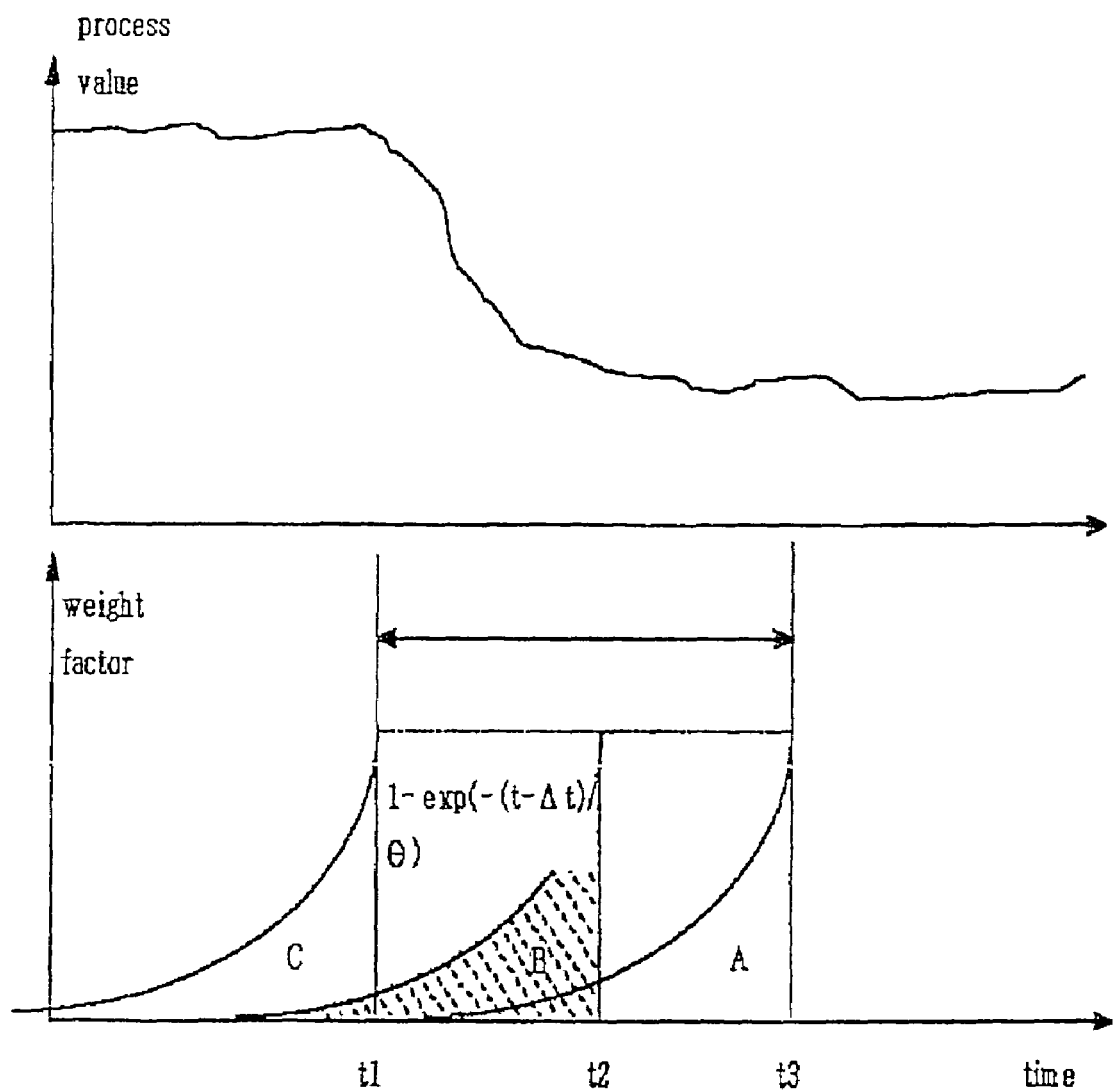
FIG. 2 is a graph, which conceptually explains the need for incorporating residence time distribution to various process variables according to the present invention, with an example of a continuous stirred tank reactor (CSTR).

FIG. 2 is a graph (case of having residence time distribution of CSTR), which conceptually explains the method incorporating the residence time distribution to the respective process variables according to the present invention. In other words, it conceptually shows the method of selecting cPV's at some instant while working with a single reactor with the reactor flow corresponding to a CSTR. The operational conditions of a product which is discharged at some instant (t) do not correspond to the operational variables at that instant (t). Rather, they correspond to the values of sum of the values of operational variables respectively multiplied by a certain weight factor from that instant to some previous point. The sum of the weight factors is 1, and accordingly the area indicated as "B" is 1. In case of a single CSTR, the formula of $1 - \exp[-(t-\Delta t)/\theta]$ is given. $\Delta t$ is a time interval from t to some previous point in time. $\theta$ is the average residence time in the reactor. Theoretically, $\Delta t$ can reach infinity, but it is generally considered up to the time interval of 3~4 times of $\theta$.

The operational conditions of a product discharged at an instant t as above do not correspond to the values of operational variables at that time t. Rather, they correspond to the values of sum of the values of operational variables respectively multiplied by a certain weight factor from that instant to some previous point. The problem caused by this inconsistency becomes more serious in case of having long residence time within a reactor, or in case of using a multi-stage reactor. To solve this problem, as shown in FIG. 1, it is necessary to employ a method of setting cPV's in the reactors by stage with respect to the final product at some instant in the multi-stage reactor.

The method of estimating the properties of a polymer product as above can also be used as a method of monitoring the state of process of the polymer product. In other words, in relation to the method of monitoring the state of process incorporating the residence time distribution to the process variables, the method of monitoring herein involves theoretically determining the amounts of content and discharge of the product in the process, and then incorporating the residence time distribution to said process variables by way of the method of solving the balance equations of a hypothetical substance by taking the process variables as those of the hypothetical substance; and monitoring the state of process by inputting to various process-state-monitoring models cPV's in the reactors by stage with respect to the final product incorporating the residence time distribution to said process variables.

Moreover, by using the method of estimating the properties of a polymer product as above, it can compute the average operational conditions appropriate for optimized operation per lot or batch of the polymer products, and it can also be used in quality control of polymer products.

Moreover, by using the method of estimating the properties of a polymer product as above for the purposes of monitoring the state of processes therein, it can compute the average operational conditions appropriate for optimized operation per lot or batch of the polymer products, and it can also be used in quality control of polymer products.

Below, the present invention as above is described in detail with an example. However, it is for illustrative purposes only and should not be deemed to limit the present invention in any manner.

FIGS. 3~7 are graphs according to one embodiment of the present invention. The process therein was a high-density polyethylene reaction process in which two reactors were connected serially.

Figure 3:
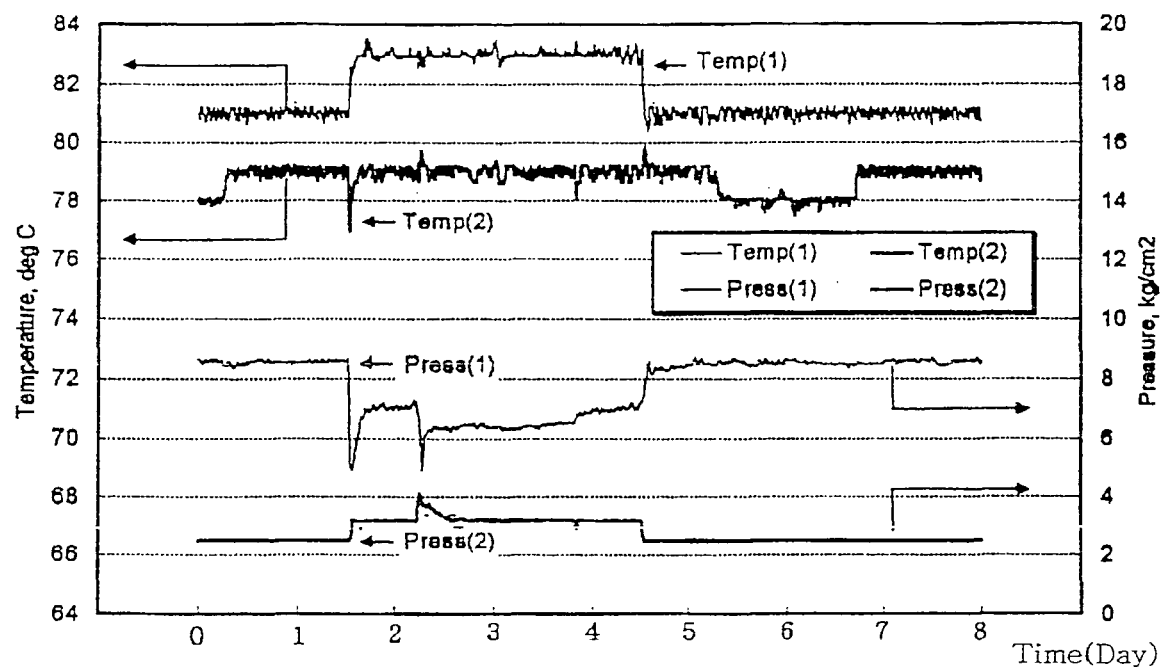
FIG. 3 is a graph, which shows the raw data of reactor temperatures and pressures as a function of time. The reactor temperature is one of the important elements in operating the reaction process of high-density polyethylene (HDPE).
Figure 4:
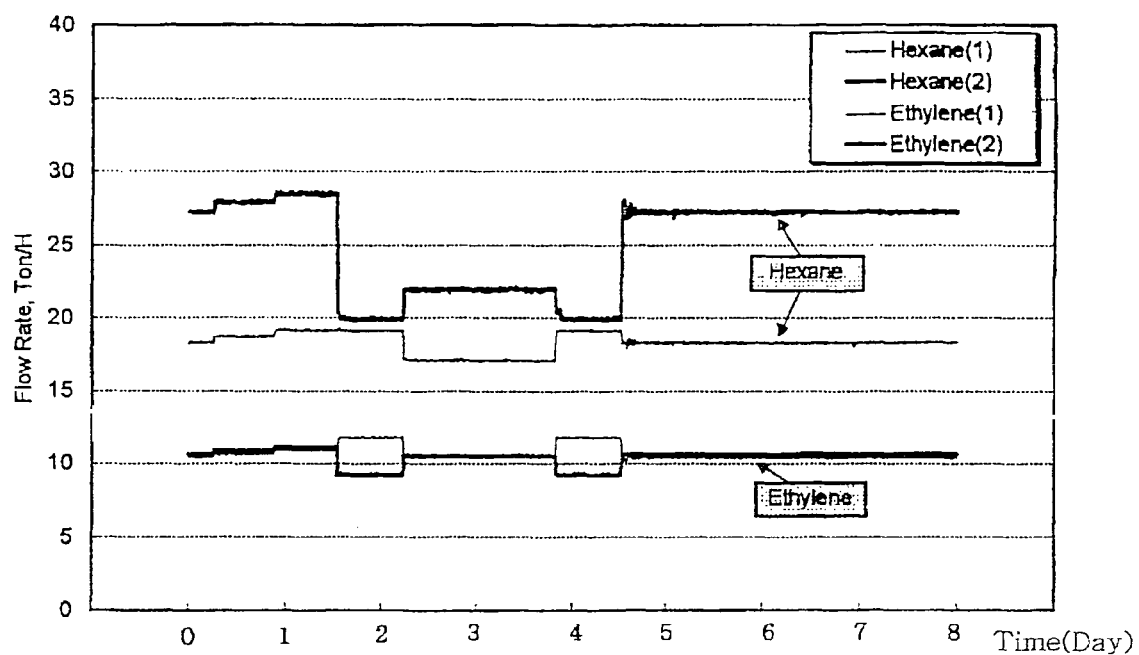
FIG. 4 is a graph, which shows the raw data of mass flow rates of ethylene and hexane into the inner chamber of a reactor as a function of time. The rate is one of the important elements in operating the reaction process of high-density polyethylene (HDPE).
Figure 5:
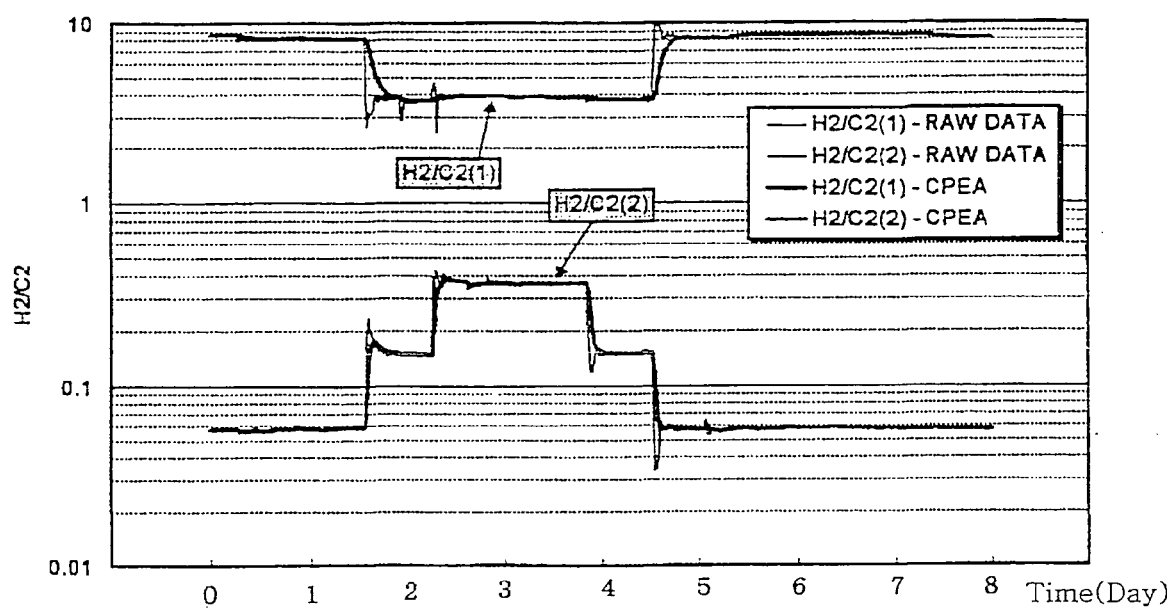
FIG. 5 is a graph, which shows the raw data of mole ratios of hydrogen and ethylene (H2/C2) and cPV's as a function of time. The mole ratio is one of the important elements in operating the reaction process of high-density polyethylene (HDPE).

FIGS. 3~5 illustrate the changes in raw data (as a function of time) of various important factors during the operation of a high-density polyethylene reaction process. FIG. 3 shows the changes in temperature and pressure within the reactor. FIG. 4 shows the changes in mass flow rates of ethylene and hexane as a function of time. There, ethylene was the main raw material flowed in to the reactor with a diluent, and hexane was used to control the residence time. Moreover, FIG. 5 respectively illustrates the raw data of mole ratios of hydrogen and ethylene ($H_2/C_2$) in gas phase within the reactor. There, hydrogen was used as an agent for controlling the molecular weights of polymers. The mole ratios of hydrogen and ethylene in gas phase were analyzed using an on-line gas chromatograph. As for the other operational conditions of the reactor, the capacities of first-stage and second-stage reactors were respectively 71 $m^3$, and the production rate of polymers was approximately 20 ton/hr. The reactor residence time for the first-stage reactor was approximately 2 hours, and approximately 1 hour for the second-stage reactor. In particular, FIG. 5 also shows cPV's as a function of time, in addition to the raw data of mole ratios of hydrogen and ethylene ($H_2/C_2$). As for the computation method of cPV's, Mathematical Formulas 10~11 as presented above were used herein. As shown in the figures, in contrast to those of the raw data, the graphs of cPV's incorporating the residence time distribution of the reactors at each stage showed a form of a very smooth curve. By inputting cPV's, not the raw data, to the empirical correlation, neural network, PLS models, etc., the properties of intermediate and final products could be thus obtained.

Figure 6:
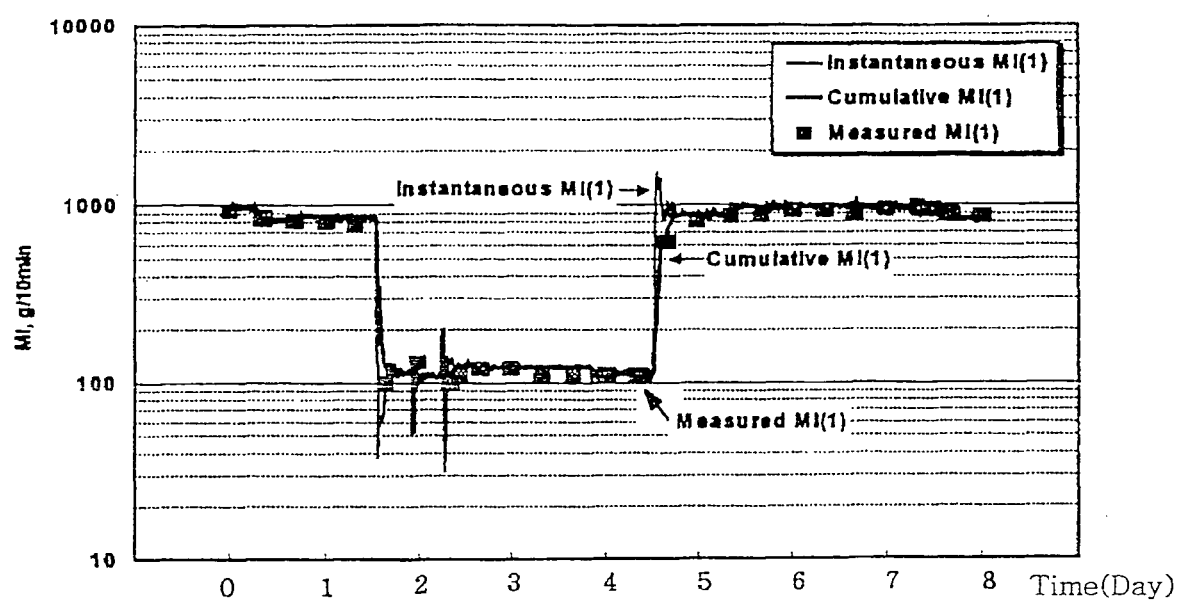
FIG. 6 is a graph, which shows the estimated values of melt index of an intermediate product as a function of time from the outlet of a first-stage reactor in the reaction process of HDPE according to the present invention.

FIG. 6 is a graph, which shows the estimated values of melt index (as a function of time) of the intermediate products at the outlet of the first-stage reactor during the HDPE reaction process according to the present invention.

Figure 7:
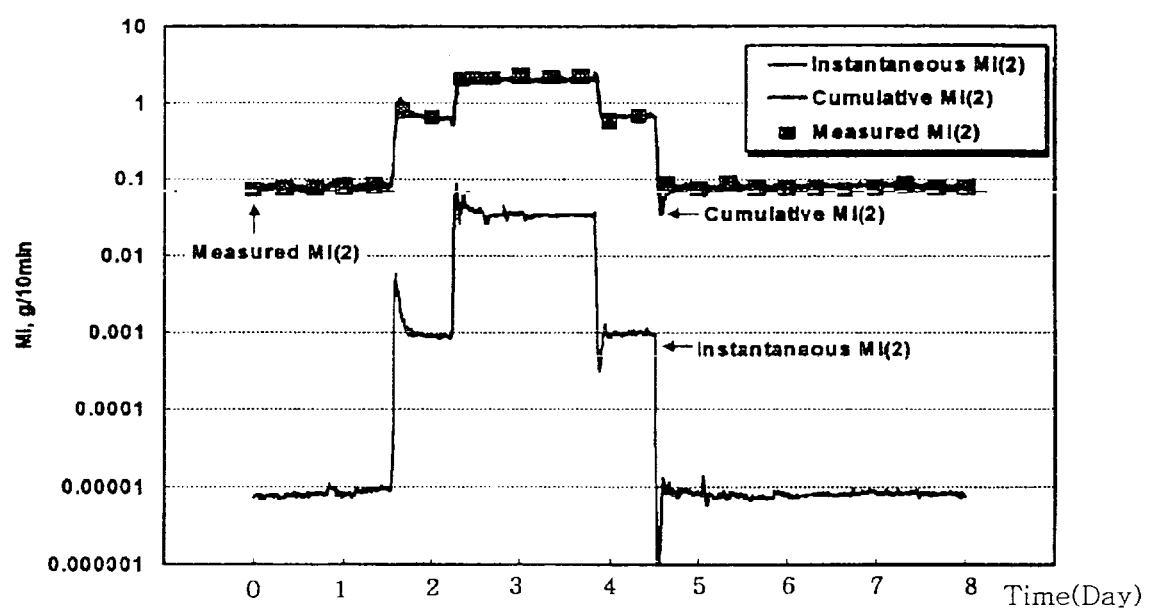
FIG. 7 is a graph, which shows the estimated values of melt index of the final product as a function of time from the outlet of a second-stage reactor in the reaction process of HDPE according to the present invention

FIG. 7 is a graph, which shows the estimated values of melt index (as a function of time) of the final products at the outlet of the second-stage reactor during the HDPE reaction process according to the present invention. For reference, it also shows the estimated values of properties (i.e., instantaneous MI) of the case in which the raw data were directly used instead of cPV's. As shown in the figure, the estimated values of properties (i.e., cumulative MI) based on cPV's have a much better fit against the actual analytical results obtained from the laboratory.

For reference, in the embodiment, the method of empirical correlation was used as a properties estimation model. The method of empirical correlation in the embodiment is one that expresses melt index of the polymers in the form of a function of temperature, pressure, and composition ratios of the substituents in the process.

According to the method of estimating the properties of a product by using cPV's in the reactors at each stage with respect to the final product, based on the present invention, it can easily estimate the properties of a polymer product from a continuous type polymerization reactor and also monitor the state of each process therein.

Moreover, according to the present invention, even with a batch or semi-batch type polymerization reactor, or in the reaction system of uneven treatment of polymers, the method can easily estimate the properties of the final product while allowing monitoring of the state of each process therein.

What is claimed is:

1. A method of estimating the properties of a polymer product comprising:

computing converted process variables (cPV's), wherein the converted process variables comprise process variables that a final product or an intermediate product experienced earlier in average in one or more reactors by stage with respect to the final product by incorporating the residence time distribution to process variables by means of theoretically determining the amounts of content and discharge of the product in the process;

solving balance equations of a hypothetical substance by taking respective process variables of the hypothetical substance; and estimating the properties of the product by inputting to various property estimation models cPV's in one or more of the reactors by stage with respect to the final product after incorporating the residence time distribution to said process variables.

2. The method of claim 1, wherein said process is a process which uses a single polymer reactor or a multi-stage polymer reactor.

3. A method of monitoring the state of process comprising:

incorporating residence time distribution to process variables, wherein said method comprises theoretically determining amounts of content and discharge of a product in the process;

incorporating the residence time distribution to the process variables by solving balance equations of a hypothetical substance by taking the respective process variables of the hypothetical substance; and monitoring the state of process therein by inputting to various process-state-monitoring models cPV's in one or more reactors by stage with respect to a final product after incorporating the residence time distribution to said process variables.

4. The method of claim 3, wherein said process is a process which uses a single polymer reactor or a multi-stage polymer reactor.

5. A method of controlling the properties of a polymer product comprising:

computing average operational conditions appropriate for optimum operation of a polymer product per lot or batch by using a method of estimating the properties of a polymer product comprising:

computing converted process variables (cPV's) wherein converted process variables comprise process variables that a final product or an intermediate product experienced earlier in average in one or more reactors by stage with respect to the final product by incorporating the residence time distribution to process variables by means of theoretically determining amounts of content and discharge of the product in the process;

solving balance equations of a hypothetical substance by taking the respective process variables of the hypothetical substance; and estimating the properties of the product by inputting to various property estimation models cPV's in one or more of the reactors by stage with respect to the final product after incorporating the residence time distribution to the process variables; and utilizing the same in quality control of the polymer product.

6. A method of controlling the properties of a polymer product comprising:

computing the average operational conditions appropriate for optimum operation of the polymer product per lot or batch by using a method of monitoring the state of process comprising:

theoretically determining amounts of content and discharge of the product in the process;

incorporating residence time distribution into process variables by solving balance equations of a hypothetical substance by taking respective process variables as those of the hypothetical substance; and monitoring the state of process therein by inputting to various process-state-monitoring models cPV's in one or more reactors by stage with respect to the final product after incorporating the residence time distribution to said process variables; and utilizing the same in quality control of the polymer product.

7. The method of claim 5, wherein said process is a process which uses a singe polymer reactor or a multi-stage polymer reactor.

8. The method of claim 6, wherein said process is a process which uses a single polymer reactor or a multi-stage polymer reactor.

* * * * *